(12) United States Patent  
Metzner et al.

(10) Patent No.: US 7,449,147 B2  
(45) Date of Patent: Nov. 11, 2008

(54) APPARATUS FOR COLLECTING IMPRINTED CASSETTES AND/OR IMPRINTED SPECIMEN SLIDES FOR HISTOLOGICAL OR CYTOLOGICAL PREPARATIONS

(75) Inventors: Holger Metzner, Nussloch (DE); Uwe Kiene, Eppelheim (DE); Manfred Biehl, Meckesheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 765 days.

(21) Appl. No.: 10/435,764

(22) Filed: May 12, 2003

(65) Prior Publication Data

US 2003/0215363 A1 Nov. 20, 2003

(30) Foreign Application Priority Data

May 18, 2002 (DE) ................................ 102 22 333

(51) Int. Cl.  
*G01N 21/00* (2006.01)

(52) U.S. Cl. ............................ 422/63; 422/64; 422/65; 422/66; 422/67; 422/99; 422/100; 436/180

(58) Field of Classification Search ............. 422/63–67, 422/99–101; 436/180  
See application file for complete search history.

(56) References Cited

U.S. PATENT DOCUMENTS

| | | | |
|---|---|---|---|
| 4,220,252 A | 9/1980 | Beall et al. | |
| 4,705,951 A * | 11/1987 | Layman et al. | ......... 250/442.11 |
| 5,821,115 A | 10/1998 | Graupner | |
| 6,099,230 A * | 8/2000 | Hitch | .................... 414/331.02 |

FOREIGN PATENT DOCUMENTS

DE 10115065 A1 10/2002

* cited by examiner

*Primary Examiner*—Jill Warden  
*Assistant Examiner*—Jyoti Nagpaul  
(74) *Attorney, Agent, or Firm*—Hodgson Russ LLP

(57) ABSTRACT

An apparatus for collecting imprinted cassettes and/or specimen slides for histological or cytological preparations comprises a motor-driven lifting platform (1) having panels (2) arranged one above another and adjustable as to height by way of the lifting platform (1), for collection of the cassettes and/or specimen slides.

9 Claims, 4 Drawing Sheets

APPARATUS FOR COLLECTING IMPRINTED CASSETTES AND/OR IMPRINTED SPECIMEN SLIDES FOR HISTOLOGICAL OR CYTOLOGICAL PREPARATIONS

CROSS REFERENCE TO RELATED APPLICATIONS

This application claims priority to German patent application 102 22 333.5, filed on May 18, 2002, which is incorporated by reference herein.

FIELD OF THE INVENTION

The invention concerns an apparatus for collecting imprinted cassettes and/or specimen slides for histological or cytological preparations.

BACKGROUND OF THE INVENTION

Unpublished German Patent Application DE 101 15 065.2 discloses an apparatus for imprinting cassettes and/or specimen slides for histological or cytological preparations in a printing system. This printing system is characterized in that the cassettes and/or specimen slides are imprinted in computer-controlled fashion by an inkjet printer, and this applied ink is then dried by way of a flash device. The flash device is followed by a removal device for depositing the imprinted cassettes and/or imprinted specimen slides. The removal device is not discussed further in this patent application.

SUMMARY OF THE INVENTION

With a high throughput of imprinted specimen slides and/or cassettes, however, it is necessary to collect these in as orderly a fashion as possible and thus make them accessible for further processing in the laboratory. It is therefore the object of the present invention to develop a printing system according to DE 101 15 065.2 in such a way that the imprinted specimen slides and/or cassettes are collected in orderly fashion.

According to the present invention, this object is achieved by way of the features disclosed and claimed herein.

The invention is characterized in that a motor-driven lifting platform having several panels arranged one above another is provided, the lifting platform carrying the panels and bringing the individual panels successively into a transfer position for collection of the specimen slides and/or cassettes.

In an embodiment of the invention, a slider device for filling the panel is provided in the transfer position for reception of a cassette and/or specimen slide.

The slider device is characterized in that a plate is provided for receiving the cassette and/or specimen slide, and from there the cassette and/or specimen slide is moved onto the panel by way of a motor-driven slider having a slider edge.

In an advantageous development of the invention, the plate is fabricated from a hardened material. This prevents the specimen slides (made of glass) from damaging the plate over time.

The invention is also characterized in that the slider has forks arranged beneath the plate. The specimen slide lies on these forks on the one hand in order to be moved onto the panel and deposited there. On the other hand, the specimen slides already lying on the panel are displaced with the fork ends in order to create room for additional specimen slides to be deposited.

In a further embodiment of the invention, provision is made for equipping the slider device with obliquely converging guides so as thereby to achieve positive centering for the specimen slide and/or cassette in the transfer position. This prevents any possible jamming of specimen slides and/or cassettes in the infeed guide.

In a development of the invention, the lifting platform is equipped with a single profiled rail having recirculating ball cages as a longitudinal guide. A commercially available component such as, for example, the NN 15-150-15/15-G3-V1 mini-rail guide with MNN 15 G3 carriage of the Schneeberger company, can be used as the profiled rail. A shaft or a spindle rotated by a motor is provided as the drive system.

In an embodiment of the invention, a sensor is associated with the lifting platform for recognition of an end position. The drive system can be shut off by way of the sensor.

In a development of the invention, a photoelectric barrier is associated with the lifting platform for recognition of the transfer position of the panel. The photoelectric barrier is triggered via a tab arranged on each panel. This association ensures that each panel is positioned by the lifting platform at the correct height and transfer position.

The invention is also characterized in that the panels have an opening. Positioned in this opening is a capacitative sensor, arranged immovably in the apparatus, that serves to recognize a specimen slide and/or cassette. The "fill level" of the panel present in the transfer position is thereby detected and another panel is moved, as applicable, by the lifting platform into the transfer position.

In a development of the invention, a base plate having centering pins is provided, on which the collection device is arranged and which serves to receive in accurately fitted fashion a printing device such as the one depicted and described in, for example, German Patent Application DE 101 15 065.2. The result of this is that the collection device is embodied as a separate and retrofittable component.

In a further embodiment of the invention, the base plate has a plug connection for electrical connection of the collection apparatus to the printing device, so that separate electrical connections for power and/or data in the collection apparatus can be dispensed with. Delivery of power is thus handled by the attached printing device.

In a further embodiment of the invention, provision is made for the individual panels to be filled in job-oriented fashion with cassettes and/or specimen slides, control of the lifting platform being accomplished via the plug connection and an attached printing device. The result of this is that several cassettes and/or specimen slides having the same imprint, or cassettes and/or specimen slides of a series, can be collected on one panel.

In a development of the invention, the plate is subdivided by a plate step into a lower step as support for the cassette, and a higher step as support for the cassette cover shaped onto the cassette. The step height in this context is approx. 6 mm.

BRIEF DESCRIPTION OF THE DRAWINGS

The invention is depicted and explained in more detail in an exemplary embodiment with reference to the schematic drawings, in which.

DETAILED DESCRIPTION OF THE INVENTION

Figure 1:
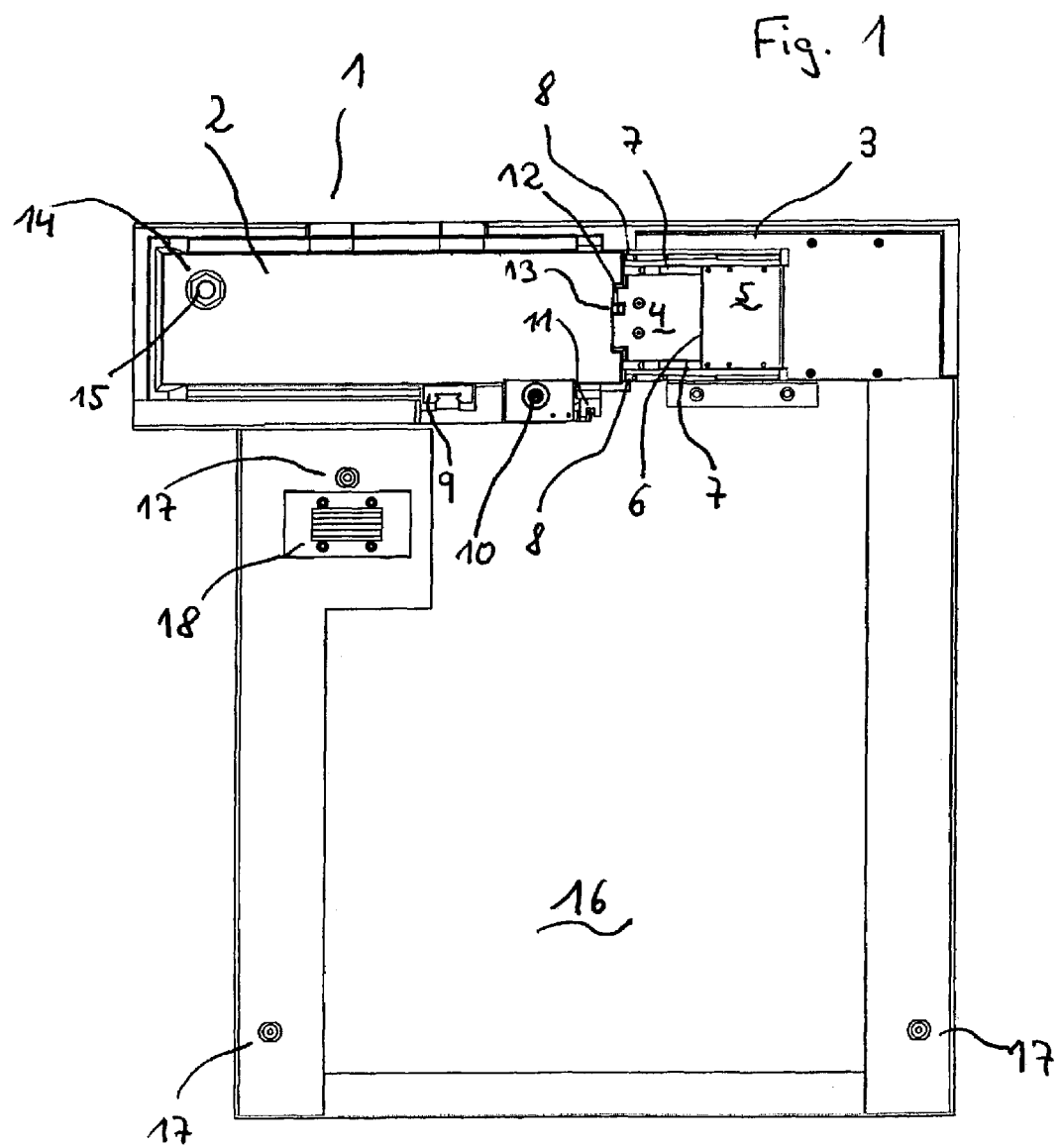
FIG. 1 is a plan view of the apparatus for collecting imprinted cassettes and/or specimen slides.
Figure 4:
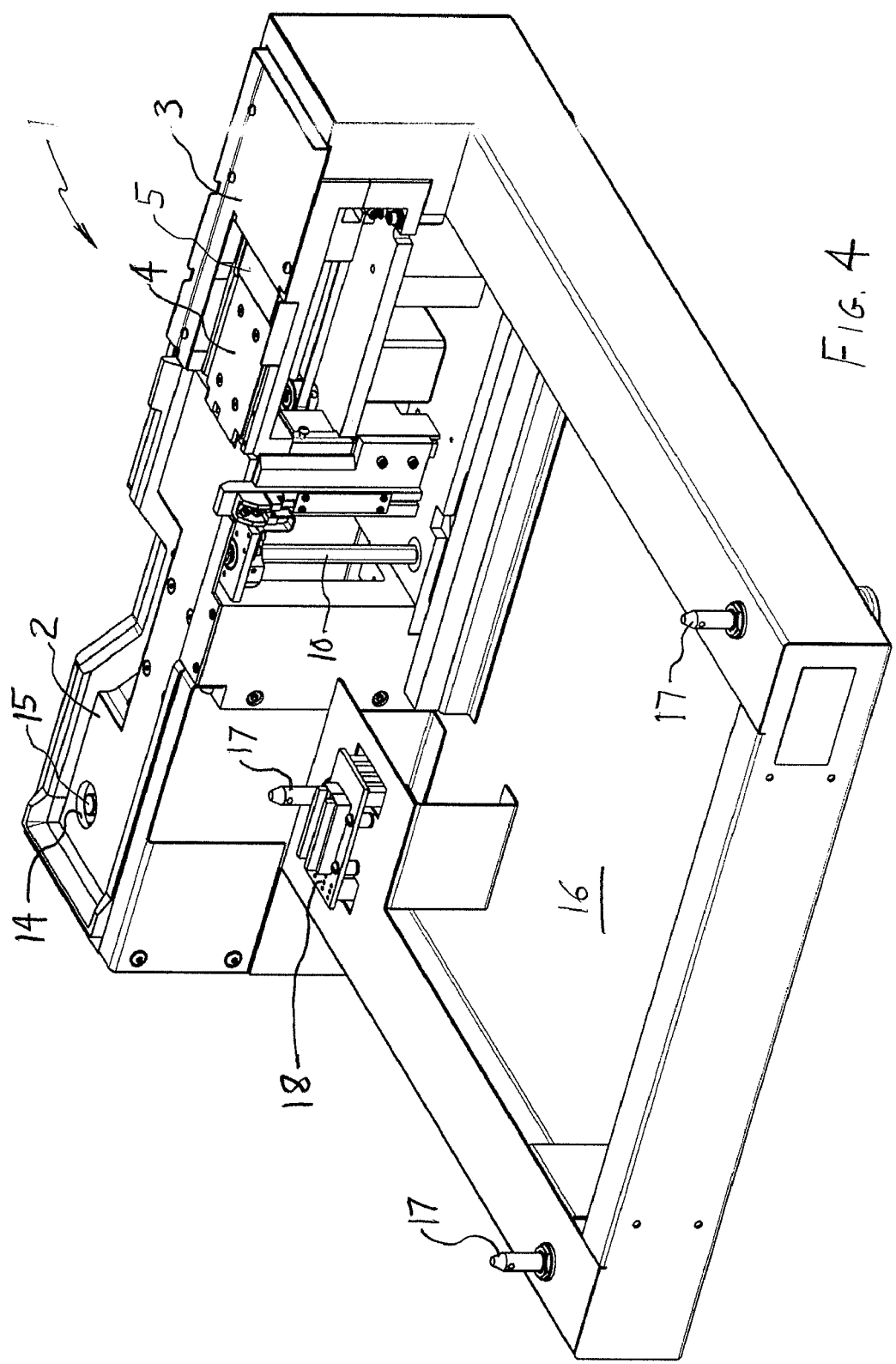
FIG. 4 is a perspective view of the apparatus shown in FIG. 1.

FIGS. 1 and 4 show an apparatus for collecting imprinted cassettes and/or specimen slides that is arranged on a base plate 16, having a lifting platform 1 on which several panels 2, arranged one above another, are provided for reception of the cassettes and/or specimen slides. A slider device 3 is equipped with a plate 4, a slider 5 that has a slider edge 6, and two forks 7 arranged on slider 5. Arranged parallel to plate 4 and opposite one another are two guides 8 with which positive centering of a cassette and/or specimen slide in the slider direction is accomplished. Plate 4 is further equipped with a photoelectric barrier 12 into which a triggering tab 13, arranged on panel 2, projects.

Lifting platform 1 has a motor-driven spindle 10 for height adjustment of panels 2 arranged one above another, and has a profiled rail 9 as guide. By way of spindle 10 and photoelectric barrier 12, the individual panels 2 can be brought into a transfer position for reception of the cassettes and/or specimen slides.

For detection of an end position, the lifting platform has a further sensor 11; when this responds, the motorized spindle drive for the lifting platform is switched off.

Lifting platform 1 furthermore has a capacitative sensor 15 that projects through an opening 14 in panel 2 and detects cassettes and/or specimen slides present in that position. By way of this sensor 15, the fill level of the panel is detected and a corresponding signal is delivered to change the panel present in the transfer position.

Base plate 16 is equipped with centering pins 17 and an electrical plug connection 18 for reception of a printing device. Centering pins 17 allow a printer to be attached in accurately fitting fashion, power delivery to and control of the collection apparatus being ensured via the plug connection by means of the attached printer.

Figure 2:
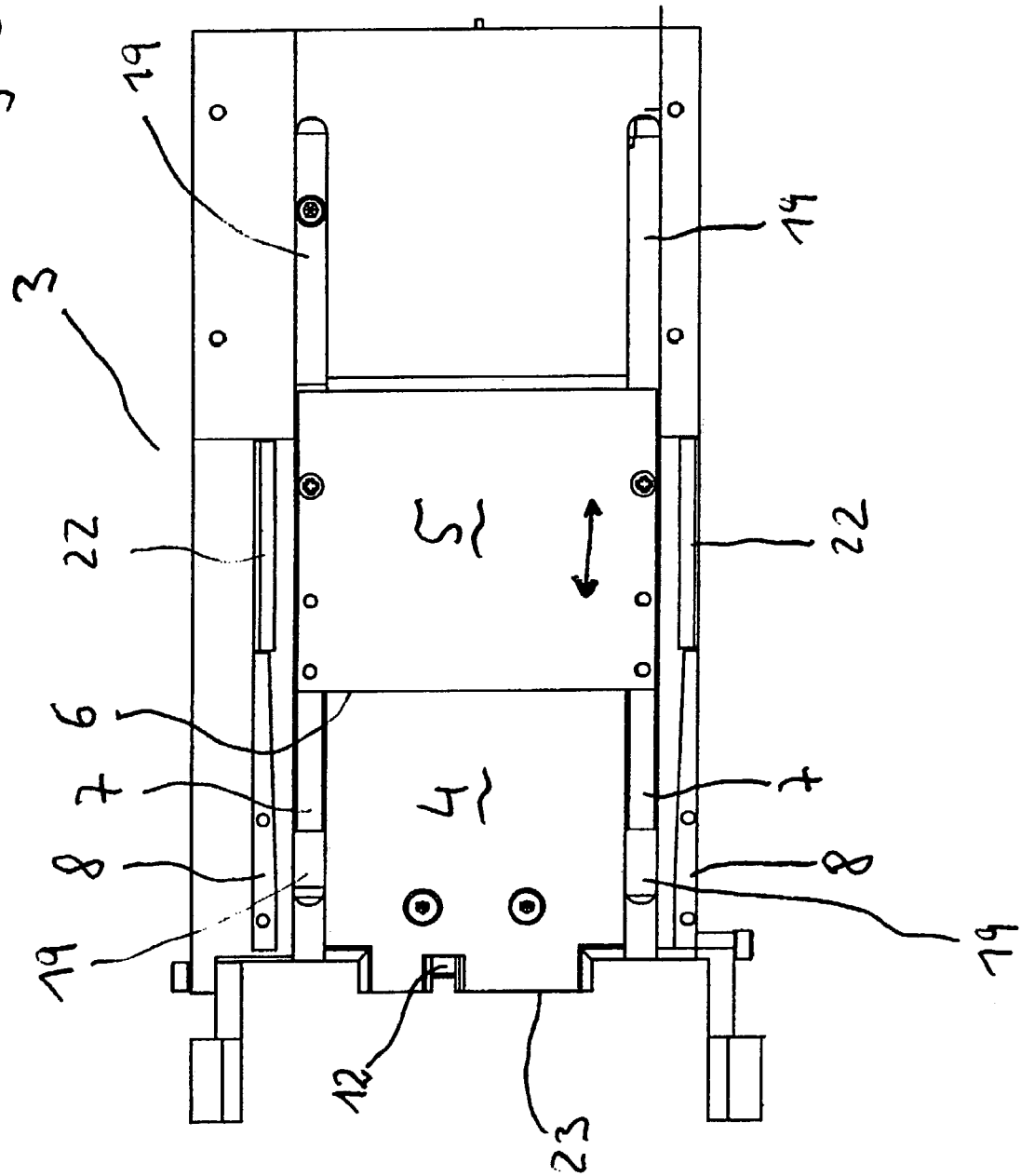
FIG. 2 is a plan view of the slider device for specimen slides.

FIG. 2 shows an enlarged portion of FIG. 1 with slider device 3. Slider device 3 here is specifically adapted for hard specimen slides made of glass. Plate 4 is fabricated from a hardened material and has a wiper edge 23 on the left side. Also shown in this depiction is a slider guide 19 on which slider 5 is moved in motorized fashion in the double-arrow direction. For reasons of simplification, the motorized drive system is not depicted.

Shown in this depiction are hardened transfer stops 22 that serve as stops for a specimen slide transferred from the printer. For transfer of a specimen slide from the printer into the collection apparatus, slider 5 is pulled completely back against the right-hand boundary of slider guide 19. Plate 4 is thereby uncovered in the region of transfer stops 22, so that a specimen slide can be transported, for example via a chute (not depicted) into the collection apparatus and comes to rest on plate 4. The specimen slide is then carried along by slider 5 with slider edge 6, and positively aligned as a result of the oblique profile of guides 8. At wiper edge 23 of plate 4, the specimen slides tip down onto forks 7 located slightly lower down, and are moved along by slider edge 6 of slider 5 until the specimen slide is resting entirely on forks 7. In this position, forks 7 are on panel 2, which is in the transfer position (FIG. 1). Slider 5 with forks 7 arranged thereon is pulled back, causing the specimen slide to be retained against wiper edge 23 and thus moved by forks 7. The specimen slide then tips down onto panel 2 (FIG. 1). The next specimen slide transferred from the printing device is also moved by slider 5 onto panel 2 (FIG. 1), the specimen slide present on panel 2 being displaced to the left by the ends of fork 7, carrying along the further specimen slides that are present. This continues until a specimen slide is detected by capacitative sensor 15 depicted in FIG. 1. When sensor 15 responds, panel 2 located lower down is moved by motor-drive spindle 10 into the transfer position. Exact positioning is accomplished via photoelectric barrier 12 and triggering tab 13 arranged on panel 2.

The transfer of a specimen slide onto the panel is complex because of the thinness of commercially available glass specimen slides (approx. 1 mm thick). Even minimal errors in the positioning of panel 2 with respect to plate 4 would inevitably result in jamming of the specimen slide and/or uncontrolled sliding of several specimen slides onto one another.

In slider device 3 depicted here, it is of course possible also to move cassettes and deposit them onto the panels, so that each panel can be individually filled with cassettes and/or specimen slides.

Figure 3:
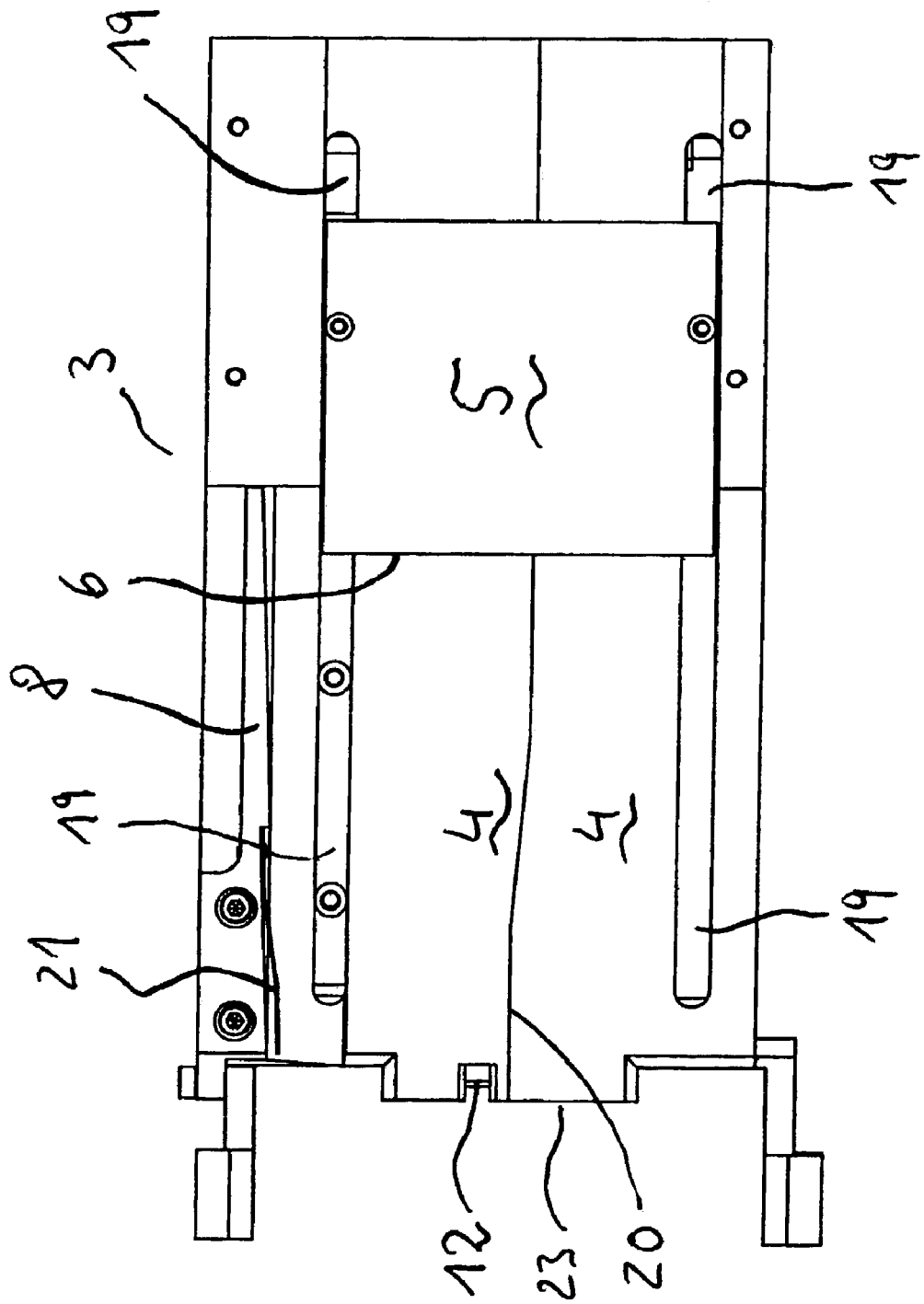
FIG. 3 is a plan view of the slider device for cassettes.

FIG. 3 shows an enlarged portion of the collection apparatus with slider device 3. Slider device 3 is here adapted specifically for plastic cassettes. These plastic cassettes are supplied selectably with and without a shaped-on cover. Exemplary embodiments of these cassettes are depicted and described in U.S. Pat. No. 5,821,115 A and U.S. Pat. No. 4,220,252.

In contrast to the exemplary embodiment of FIG. 2, plate 4 is configured by way of a plate step 20 into a lower step for reception of the cassette and an upper (higher) step for the cover shaped onto the cassette. Plate step 20, and guide 8 opposite, converge obliquely, thereby forming a positive guide for the cassettes. Guide 8 has at its left end a spring 21 so that cassettes of different dimensions can be reliably guided.

Since, in contrast to the specimen slides, the thickness of the cassettes is greater than 5 mm, slight tolerances in the positioning of panels 2 with respect to the wiper edge are permissible, and the forks on slider 5 can be dispensed with. Panels 2 are positioned in such a way that their upper edge lies slightly below plate 4, so that cassettes with or without a cover can be pushed by slider edge 6 of slider 5 over wiper edge 23, tipped down there, and pushed to the left onto the cassettes present on panel 2. Here as well, a full panel 2 is detected via sensor 15.

PARTS LIST

1 Lifting platform
2 Panel
3 Slider device
4 Plate
5 Slider
6 Slider edge
7 Fork
8 Guides
9 Profiled rail
10 Spindle
11 Sensor
12 Photoelectric barrier
13 Triggering tab
14 Opening in (2)
15 Capacitative sensor
16 Base plate
17 Centering pin
18 Plug connection
19 Slider guide
20 Plate step
21 Spring
22 Transfer stop
23 Wiper edge

What is claimed is:

1. An apparatus for collecting imprinted specimen slides and/or cassettes for histological or cytological preparations comprising:

a motor-driven lifting platform;

a plurality of panels arranged one above another on the lifting platform for respectively receiving a specimen slide or cassette;

wherein the lifting platform moves the plurality of panels to bring an individual panel into a transfer position; and a slider device associated with the transfer position for receiving a specimen slide or cassette and transferring the received specimen slide or cassette to the individual panel in the transfer position;

wherein the slider device includes a plate for receiving a specimen slide or cassette, and a slider having a slider edge for transferring the received specimen slide or cassette onto the individual panel in the transfer position;

wherein the slider device further has forks arranged beneath the plate for transferring the received specimen slide or cassette onto the individual panel in the transfer position.

2. An apparatus for collecting imprinted specimen slides and/or cassettes for histological or cytological preparations comprising:

a motor-driven lifting platform;

a plurality of panels arranged one above another on the lifting platform for respectively receiving a specimen slide or cassette;

wherein the lifting platform moves the plurality of panels to bring an individual panel into a transfer position; and a slider device associated with the transfer position for receiving a specimen slide or cassette and transferring the received specimen slide or cassette to the individual panel in the transfer position;

wherein the slider device includes guides having obliquely converging surfaces arranged on opposite sides of the plate for centering the specimen slide or cassette being transferred onto the individual panel in the transfer position.

3. An apparatus for collecting imprinted specimen slides and/or cassettes for histological or cytological preparations comprising:

a motor-driven lifting platform;

a plurality of panels arranged one above another on the lifting platform for respectively receiving a specimen slide or cassette;

wherein the lifting platform moves the plurality of panels to bring an individual panel into a transfer position; and a slider device associated with the transfer position for receiving a specimen slide or cassette and transferring the received specimen slide or cassette to the individual panel in the transfer position;

wherein the slider device includes a plate for receiving a specimen slide or cassette, and a slider having a slider edge for transferring the received specimen slide or cassette onto the individual panel in the transfer position;

wherein the plate includes a photoelectric barrier and each of the plurality of panels includes a tab arranged to project into the photoelectric barrier when the panel is in the transfer position.

4. An apparatus for collecting imprinted specimen slides and/or cassettes for histological or cytological preparations comprising:

a motor-driven lifting platform;

a plurality of panels arranged one above another on the lifting platform for respectively receiving a specimen slide or cassette;

wherein the lifting platform moves the plurality of panels to bring an individual panel into a transfer position; and a base plate defining a space adjacent the lifting platform and including centering pins for receiving and positioning a removable printing device in the defined space, wherein the lifting platform is supported on the base plate and the removable printing device can be supported and positioned on the base plate adjacent the lifting platform, and the base plate further includes a plus connection for electrical connection between the apparatus and the removable printing device received in the defined space.

5. The apparatus of claim 4, wherein the motor-driven lifting platform comprises a spindle for moving the plurality of panels and a profiled rail for guiding movement of the plurality of panels.

6. The apparatus of claim 4, wherein the motor-driven lifting platform further comprises a sensor for sensing an end position of the plurality of panels.

7. The apparatus of claim 4, wherein the motor-driven lifting platform is controlled by the printing device via the plug connection, whereby a plurality of specimen slides or cassettes having the same imprint can be transferred onto a common one the plurality of panels.

8. The apparatus of claim 4, further comprising a slider device associated with the transfer position for receiving a specimen slide or cassette and transferring the received specimen slide or cassette to the individual panel in the transfer position.

9. The apparatus of claim 4, wherein the slider device includes a plate for receiving a specimen slide or cassette, and a slider having a slider edge for transferring the received specimen slide or cassette onto the individual panel in the transfer position.

* * * * *